(12) United States Patent
da Conceição Moutinho et al.

(10) Patent No.: US 12,226,653 B2
(45) Date of Patent: *Feb. 18, 2025

(54) URINARY CATHETER FOR DETECTING RADIATION

(71) Applicant: NU-RISE Lda, Ilhavo (PT)

(72) Inventors: Luis Miguel da Conceição Moutinho, Aveiro (PT); Joana Isabel Ferreira dos Santos Melo, Aveiro (PT)

(73) Assignee: NU-RISE Lda (PT)

( * ) Notice: Subject to any disclaimer, the term of this patent is extended or adjusted under 35 U.S.C. 154(b) by 0 days.

This patent is subject to a terminal disclaimer.

(21) Appl. No.: 18/541,038

(22) Filed: Dec. 15, 2023

(65) Prior Publication Data

US 2024/0115879 A1 Apr. 11, 2024

Related U.S. Application Data

(63) Continuation of application No. 17/236,089, filed on Apr. 21, 2021, now Pat. No. 11,896,844, which is a
(Continued)

(51) Int. Cl.
*A61N 5/10* (2006.01)
*A61M 25/10* (2013.01)
*G01T 1/20* (2006.01)

(52) U.S. Cl.
CPC .......... *A61N 5/1002* (2013.01); *A61M 25/10* (2013.01); *G01T 1/2002* (2013.01);
(Continued)

(58) Field of Classification Search
CPC ...... A61B 5/0036; A61B 5/055; A61M 25/10; A61M 2025/1079; A61N 5/1007;
(Continued)

(56) References Cited

U.S. PATENT DOCUMENTS

| 1,662 A | * | 6/1840 | Norris | G09B 29/02 |
| | | | | 434/150 |
| 10,293,178 B2 | * | 5/2019 | De Vries | A61N 5/1075 |

(Continued)

FOREIGN PATENT DOCUMENTS

| EP | 3031494 A1 | 6/2016 |
| WO | 2013012331 A1 | 1/2013 |
| WO | 2016093942 A2 | 6/2016 |

OTHER PUBLICATIONS

Int'l Search Report and Written Opinion Appln No. PCT/IB2022/053685 mailed Aug. 30, 2022.
(Continued)

*Primary Examiner* — Jeffrey G Hoekstra
*Assistant Examiner* — Gabriel Victor Popescu
(74) *Attorney, Agent, or Firm* — McAndrews, Held & Malloy, Ltd.

(57) ABSTRACT

Interstitial brachytherapy is a cancer treatment in which radioactive material is placed directly in the target tissue of the affected site using an afterloader. The accuracy of this placement is monitored in real time using a urinary catheter that locates the radioactive material according to the radiation levels measured by sensors in the walls of the urinary catheter. A scintillator that is embedded in the walls of the urinary catheter produces light when irradiated by the radioactive material. This light is proportional to the level of radiation at each location. The light produced by each scintillator is carried through optical fibers and then converted to an electrical signal that is proportional to the light and the radiation level at each location. The radioactive material is located according to the plurality of electrical signals. This location can be used as quality control feedback to the afterloader.

20 Claims, 8 Drawing Sheets

Related U.S. Application Data continuation-in-part of application No. 16/713,530, filed on Dec. 13, 2019, now Pat. No. 11,903,672.

(52) U.S. Cl.
 CPC ............ *G01T 1/2006* (2013.01); *G01T 1/201* (2013.01); *A61M 2025/1079* (2013.01); *A61N 2005/1003* (2013.01); *A61N 2005/1008* (2013.01); *A61N 2005/1051* (2013.01)

(58) Field of Classification Search
 CPC .......... A61N 5/1027; A61N 2005/1008; A61N 2005/1051; A61N 5/1014; A61N 5/1049; G01T 1/2002; G01T 1/2006
 See application file for complete search history.

(56) References Cited

U.S. PATENT DOCUMENTS

| | | | |
|---|---|---|---|
| 11,896,844 B2* | 2/2024 | da Conceicao Moutinho | ............ A61N 5/1002 |
| 11,903,672 B2* | 2/2024 | da Conceicao Moutinho | ............ A61N 5/1049 |
| 2002/0087079 A1* | 7/2002 | Kaufman | ............. A61B 6/4258 600/436 |
| 2010/0010343 A1* | 1/2010 | Daghighian | ......... A61B 6/4233 600/436 |
| 2010/0288934 A1* | 11/2010 | Keppel | ................... G01T 1/205 250/362 |
| 2014/0051968 A1* | 2/2014 | Isham | .................. A61N 5/1031 600/407 |
| 2016/0310759 A1* | 10/2016 | D'Andrea | ............ A61N 5/1016 |
| 2017/0304652 A1 | 10/2017 | Belley et al. | |
| 2020/0041660 A1 | 2/2020 | Isham et al. | |

OTHER PUBLICATIONS

Moutinho L M et al: "Scintillating fiber optic dosimeters for breast and prostate brachytherapy", Progress in Biomedical Optics and Imaging, SPIE—International Society for Optical Engineering, Bellingham, WA, US, vol. 10058, Feb. 28, 2017 (Feb. 28, 2017), pp. 100580C-100580C, XP060084179, ISSN: 1605-7422, DOI: 10.1117/12.2254397 ISBN: 978-1-5106-0027-0.

Luc Beaulieu et al: "Review of plastic and liquid scintillation dosimetry for photon, electron, and proton therapy", Physics in Medicine and Biology, Institute of Physics Publishing, Bristol GB, vol. 61, No. 20, Oct. 3, 2016 (Oct. 3, 2016), XP020309587, ISSN: 0031-9155, DOI: 10.1088/0031-9155/61/20/R305 [retrieved on Oct. 3, 2016].

Int'l Search Report and Written Opinion Appln No. PCT/US2020/001028 mailed May 3, 2021.

\* cited by examiner

URINARY CATHETER FOR DETECTING RADIATION

PRIORITY CLAIM

The present application is a continuation of U.S. application Ser. No. 17/236,089, filed Apr. 21, 2021, which is a continuation of U.S. application Ser. No. 16/677,866, filed Nov. 8, 2019, now U.S. Pat. No. 11,095,996, which makes reference to, claims priority to, and claims benefit from provisional patent application 62/758,077, filed on Nov. 9, 2018. The aforementioned documents are hereby incorporated herein by reference in their entirety.

BACKGROUND

Limitations and disadvantages of conventional approaches to data storage will become apparent to one of skill in the art, through comparison of such approaches with some aspects of the present method and system set forth in the remainder of this disclosure with reference to the drawings.

BRIEF SUMMARY

A urinary catheter is provided for detection and tracking of a radiation dose in radiotherapy substantially as illustrated by and/or described in connection with at least one of the figures, as set forth more completely in the claims.

DETAILED DESCRIPTION

Brachytherapy is commonly used as an effective treatment for cervical, prostate, breast, esophageal and skin cancer, and can also be used to treat tumors in many other body sites. Interstitial brachytherapy is a cancer treatment in which radioactive material is placed directly in the target tissue of the affected site, such as the prostate or breast.

The dose rate of brachytherapy refers to the level or intensity with which the radiation is delivered to the surrounding medium and can be expressed in Grays per hour (Gy/h). In high-dose rate (HDR) brachytherapy, the rate of dose delivery typically exceeds 12 Gy/h. During HDR brachytherapy, a radiation source is placed for a set duration (usually a number of minutes or hours) before being withdrawn. The specific treatment duration depends on many different factors, including the required rate of dose delivery and the type, size and location of the cancer.

A range of imaging technologies (e.g., x-ray radiography, ultrasound, computed axial tomography (CT or CAT) scans and magnetic resonance imaging (MRI)) can be used to visualize the shape and size of the tumor and its relation to surrounding tissues and organs. The data from many of these sources can be used to create a 3D map of the tumor and the surrounding tissues. Using this information, a plan of the optimal distribution of the radiation sources can be developed. This includes consideration of how the radiation should be placed and positioned. Errors or poor treatment setup might present a safety risk to the patient. Too little irradiation or too much irradiation must be avoided during treatment, as these can result in treatment failure and severe side-effects.

Figure 1:
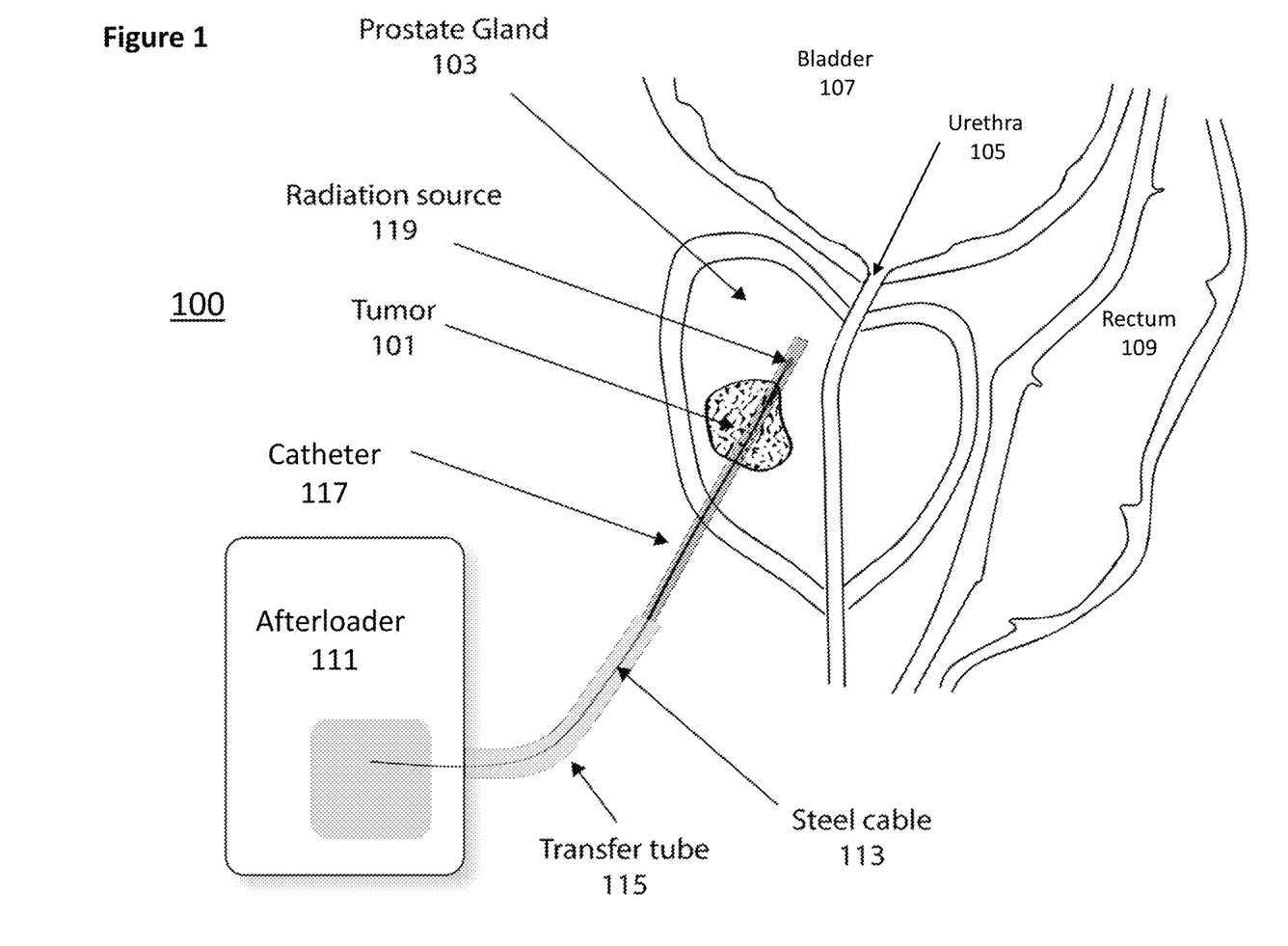
FIG. 1 illustrates an example interstitial brachytherapy treatment using an afterloader directed at a tumor in a patient's prostrate in accordance with aspects of this disclosure.

FIG. 1 illustrates an example interstitial brachytherapy treatment of a tumor 101 in a patient's prostate gland 103 in accordance with aspects of this disclosure. The size and location of the tumor 101 relative to the patient's urethra 105, bladder 107 and rectum 109 as shown is for illustration purposes. The tumor 101 may be any size and located anywhere in the prostate 103.

As shown in FIG. 1, an afterloader 111 is a radiotherapy machine being used to control the HDR brachytherapy treatment of the tumor 101. A transfer tube 115 connects from the afterloader 111 to a plastic or metallic catheter 117. The transfer tube 115 is designed to take the steel cable 113 with the radioactive source 119 from the afterloader 111 to the catheter 117. The catheter 117 receives the radiation source 119, and the afterloader 111 controls the movement, positioning and dwell time of the radiation source 119 within the tumor 101 as specified by a doctor's treatment plan.

Interstitial brachytherapy requires the precise placement of short-range radiation sources 119 (e.g., radioisotopes Cobalt-60, Iodine-125, Cesium-131, Iridium-192, etc.) closely to the site of a cancerous tumor 101. Radiation treatment is intended to kill cancerous tissue while reducing exposure to healthy tissues. The radiation source 119 may travel throughout the catheter 117 length, while stopping at predetermined periods in specific positions, thus providing irradiation of the surrounding tissues of the tumor 101 in an isotropic way. However, if the afterloader is not properly calibrated, healthy (e.g., non-cancerous) tissues may be irradiated in error.

Figure 2:
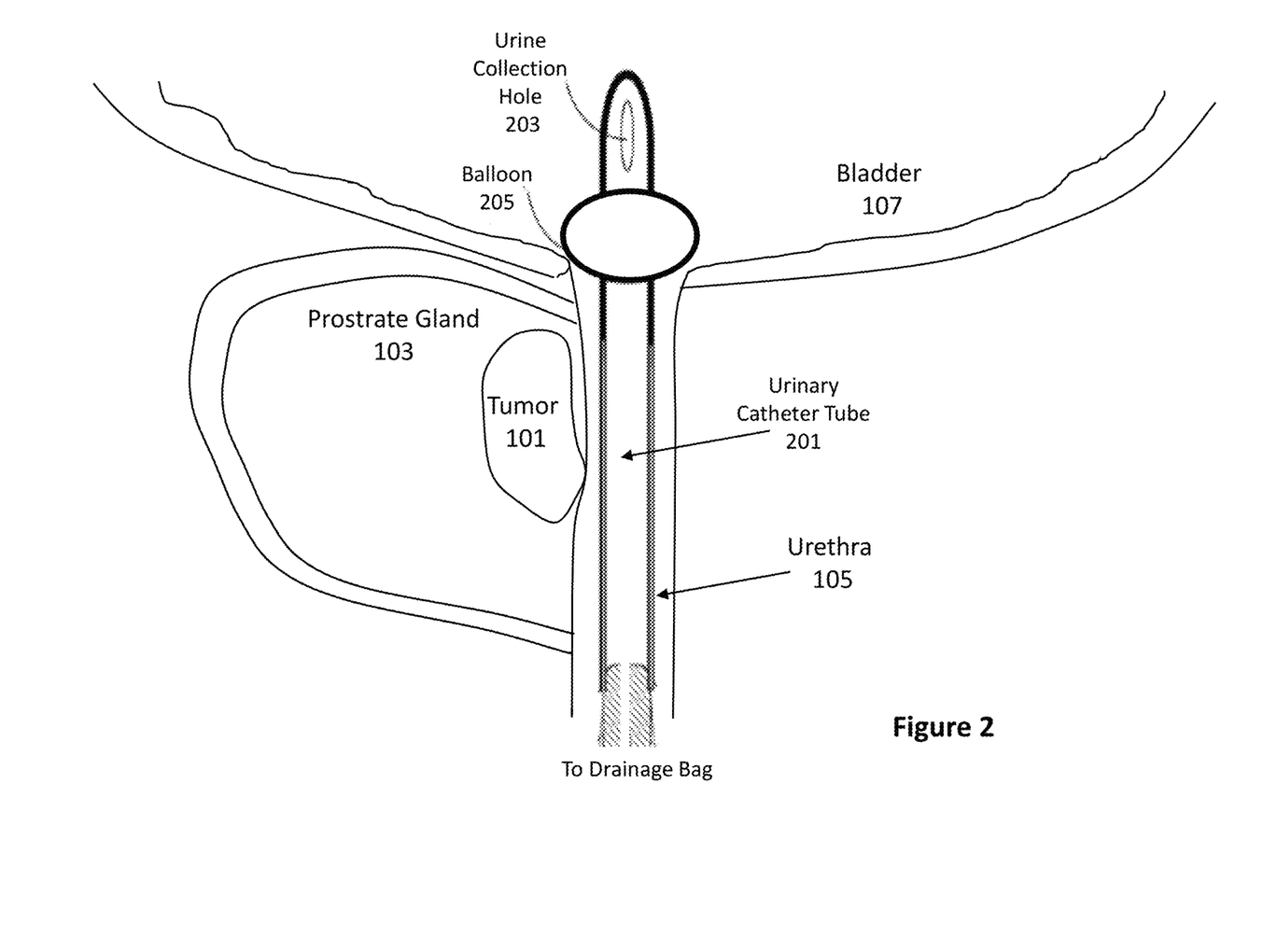
FIG. 2 illustrates the placement of an exemplary urinary catheter in accordance with aspects of this disclosure.

Aspects of the present disclosure provide a urinary catheter that is operable to detect and locate a radiation source. FIG. 2 illustrates the placement of an exemplary urinary catheter in accordance with aspects of this disclosure. The urinary catheter tube 201 is located in the urethra. One end of the tube 201 comprises a urine collection hole 203 that is inserted into the bladder 107. This end of the tube is held in place with an inflatable balloon 205 at the neck of the bladder 107. The other end of the tube 201 is connected to an external drainage bag.

Figure 3A:
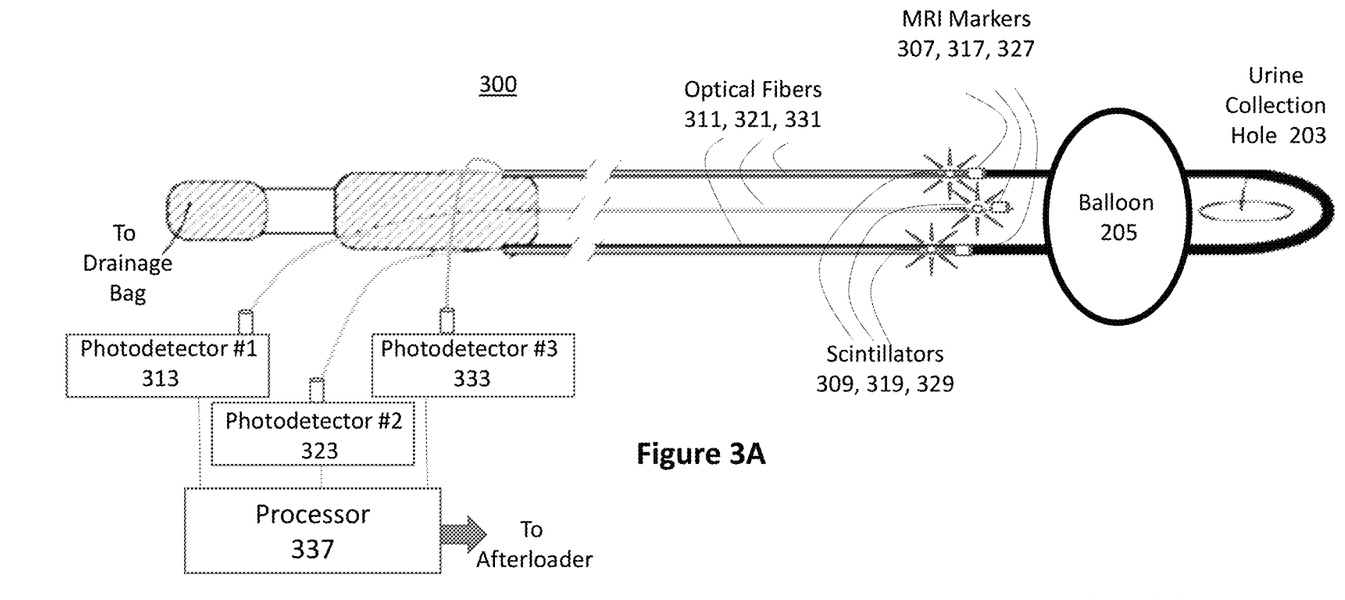
FIG. 3A illustrates an exemplary urinary catheter for measuring radiation in accordance with aspects of this disclosure.

FIG. 3A illustrates an exemplary urinary catheter 300 for measuring radiation in accordance with aspects of this disclosure. A plurality of radiation sensors are embedded in the walls of the urinary catheter tube 201. Each radiation sensor comprises a fiducial marker 307, 317, 327, a scintillator 309, 319, 329, and an optical fiber 311, 321, 331. Each fiducial marker 307, 317, 327 may comprise a gold tip that allows each radiation sensor to be located with an MRI scanner. Each fiducial marker 307, 317, 327 may be cylindrical and 1 mm or less. The plurality of MRI markers may be located via an MRI machine after the urinary catheter is placed in a patient and prior to radiation therapy.

Each scintillator 309, 319, 329 collects radiation and converts this radiation into a luminous signal with an intensity that is proportional to the level of incident radiation. The scintillator may be and inorganic or organic with cylindrical shape or organic scintillating optical fiber, matching the sectional shape and dimension of the optical fiber 311, 321, 331. For example, each scintillators 309, 319, 329 may comprise a scintillating, multi-clad optical fiber with 0.5 mm diameter (e.g., Saint-Gobain BCF-12). The fiducial marker 307, 317, 327 may have the same diameter as the optical fiber. Each optical fiber 311, 321, 331 allows the light of the corresponding luminous signal to be carried to a light detection unit (e.g., photodetector, photodiode) of a plurality of light detection units 313, 323, 335 that can be located external to the patient. Each light detection unit 313, 323, 333 is configured to produce an electrical signal in a presence of the light from one scintillator of the plurality of scintillators 309, 319, 329. The level of the electrical signal produced by each light detection unit 313, 323, 333 is proportional to the light incident to each light detection unit 313, 323, 333. Thus the level of the electrical signal produced by each light detection unit 313, 323, 333 is proportional to the level of the radiation incident to each scintillator 309, 319, 329. Each light detection unit of the plurality of light detection units 313, 323, 333 may be located near coupled to one scintillator of the plurality of scintillators 309, 319, 329 via an optical fiber.

A processor 337 is configured to calculate a location of the radiation source according to the electrical signals from the plurality of light detection units 313, 323, 333. The processor 337 may be configured to calculate the location of the radiation source by triangulation according to the electrical signals from the plurality of light detection units 313, 323, 333. The processor may also be configured to calculate a velocity of the radiation source 119 according to the electrical signals from the plurality of light detection units.

Figure 3B:
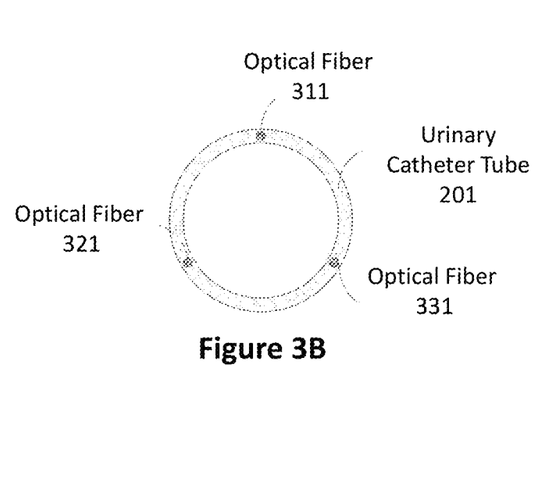
FIG. 3B illustrates a cutaway view of an exemplary urinary catheter for measuring radiation in accordance with aspects of this disclosure.

FIG. 3B illustrates a cutaway view of an exemplary urinary catheter for measuring radiation in accordance with aspects of this disclosure. In this cutaway view, optical fiber 311, 321, 331 are shown to be equally spaced around the urinary catheter tube 201.

Figure 4A:
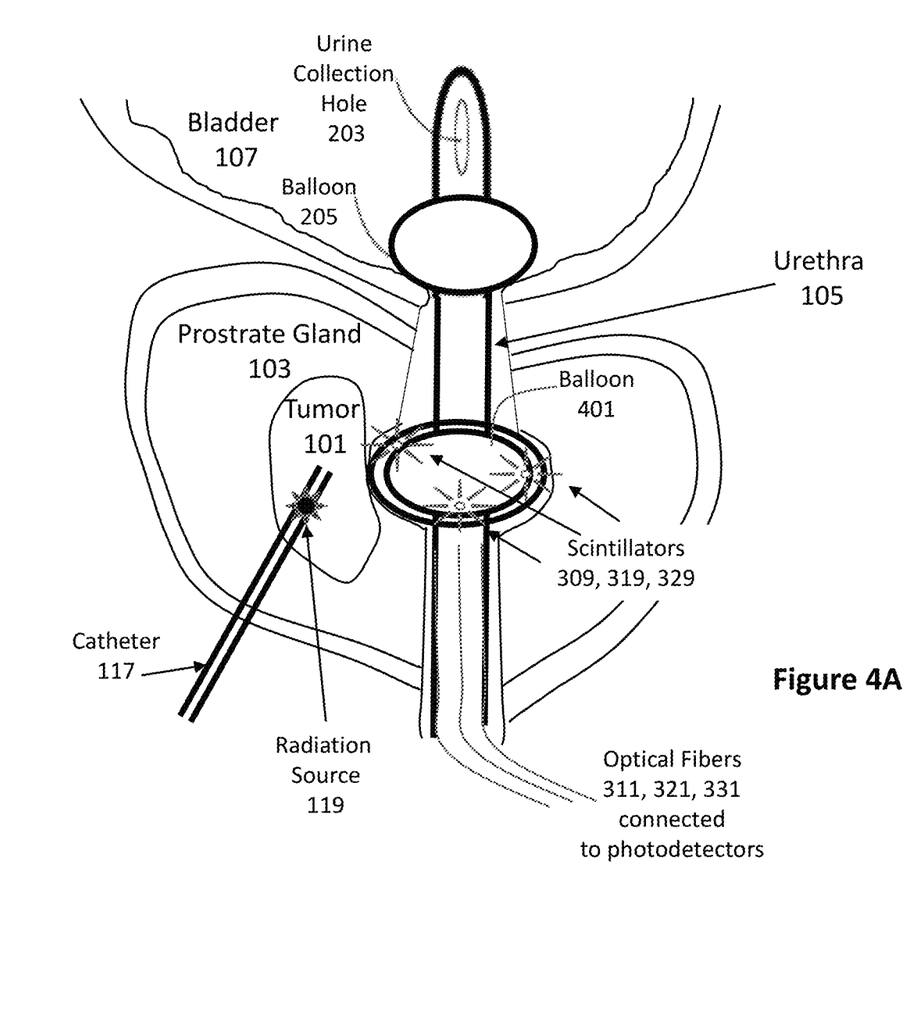
FIG. 4A illustrates the placement of an exemplary urinary catheter in accordance with aspects of this disclosure.

FIG. 4A illustrates the placement of an exemplary urinary catheter in accordance with aspects of this disclosure. In FIG. 4A, the tumor 101 is irradiated by a radiation source 119 that is placed within the tumor 101 by an afterloader catheter 117. The urinary catheter may comprise a second balloon 401 that can expand the urinary catheter tube to be closer to the tumor 101. The scintillators 309, 319, 329 may be located around this balloon 401 and also be relocated. For example, the plurality of scintillators 309, 319, 329 and the plurality of optical fibers 311, 321, 331 may be spread out when the balloon 401 is expanded. The exact position of the scintillators 309, 319, 329 may be determined via a CT scan or MRI before the radiation begins by mapping the fiducial markers 307, 317, 327.

Figure 4B:
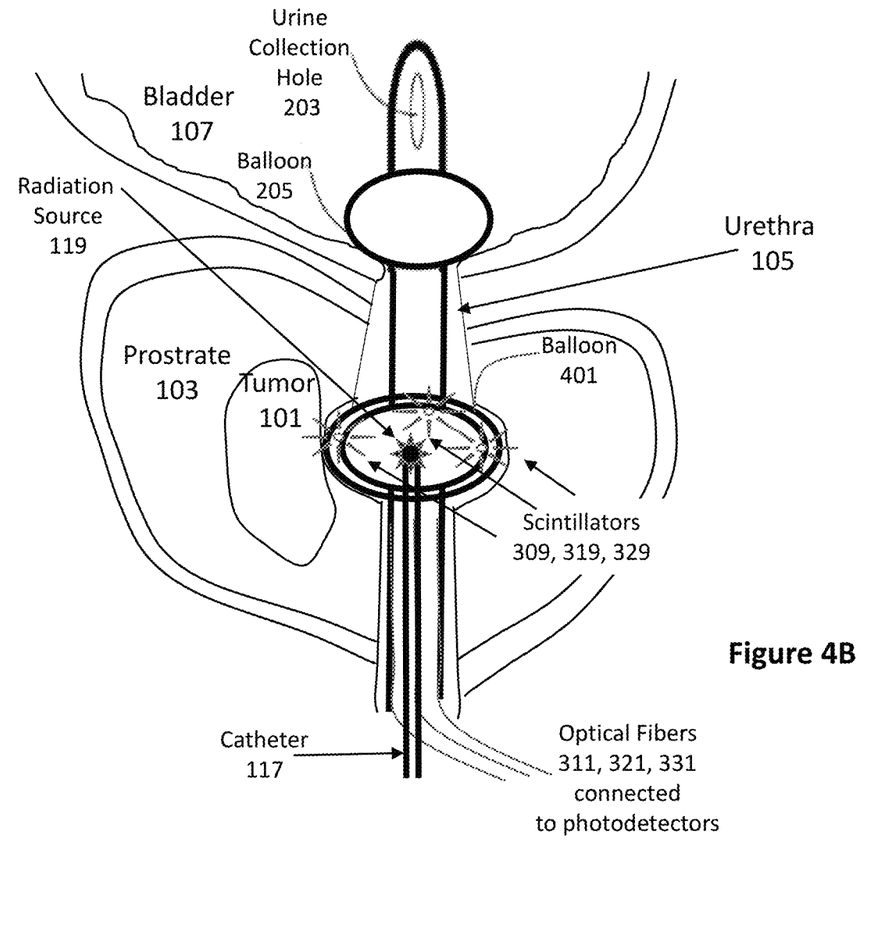
FIG. 4B illustrates another placement of an exemplary urinary catheter in accordance with aspects of this disclosure.

FIG. 4B illustrates another placement of an exemplary urinary catheter in accordance with aspects of this disclosure. In FIG. 4B, the tumor 101 is irradiated by a radiation source 119 that is placed within the urethra 105 by an afterloader catheter 117 within the urinary catheter. With the second balloon 401 inflated, radiation can reach the tumor 101 without directly injecting the afterloader catheter 117 into the tumor 101. The afterloader catheter 117 may also be integrated into the catheter tube 201.

The electrical signals produced by external photodetectors may be processed to triangulate the position of a radiation source 119. The urinary catheter can therefore be used to track the afterloader on a real-time basis. This location as determined by the urinary catheter system can be used as quality control feedback to the afterloader. The urinary catheter, with or without the afterloader catheter 117, may be disposable.

Figure 5A:
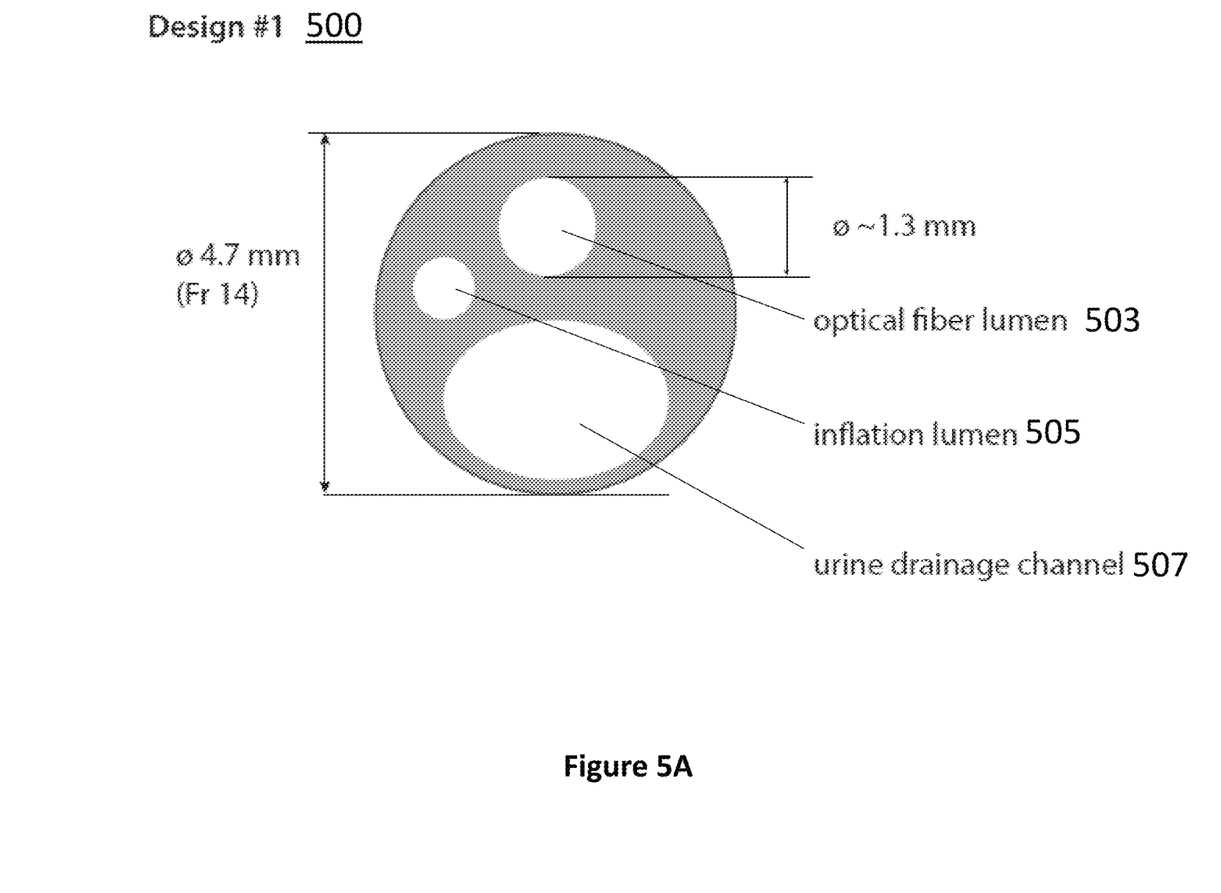
FIGS. 5A, 5B and 5C illustrate cutaway views of alternative exemplary urinary catheters for measuring radiation in accordance with aspects of this disclosure.
Figure 5B:
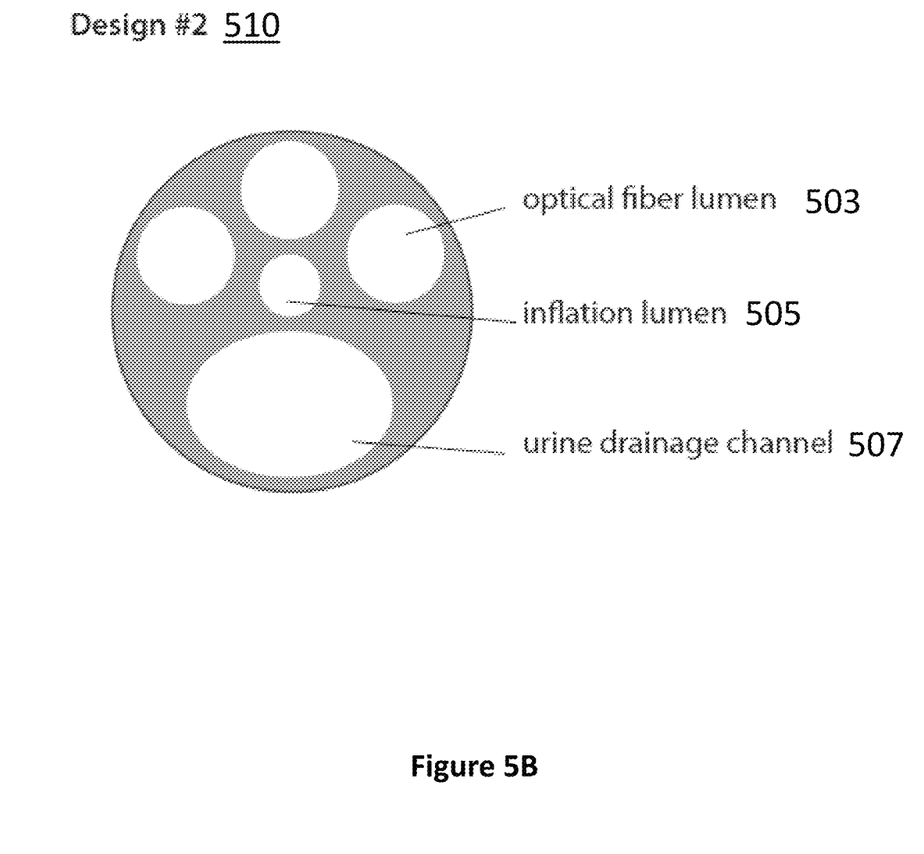
Figure 5C:
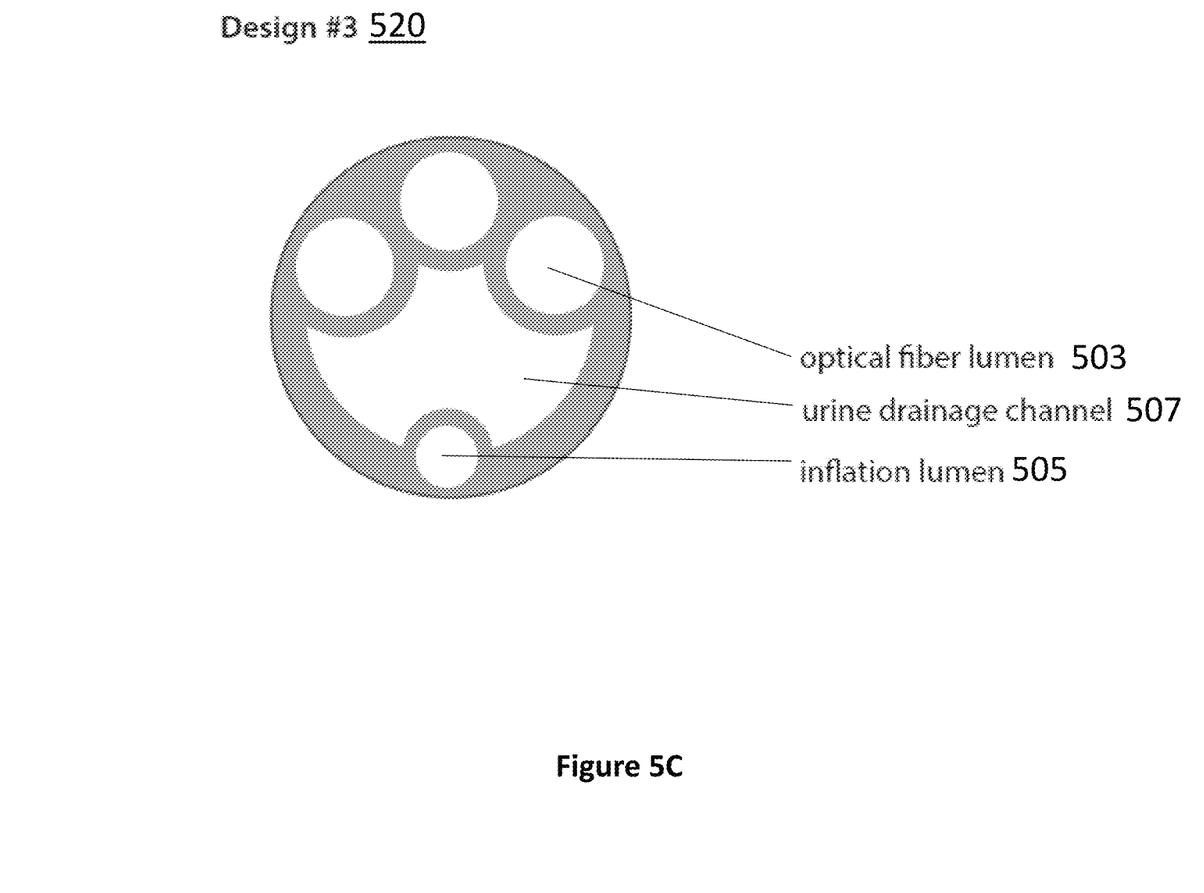

FIGS. 5A, 5B and 5C illustrate cross-section/cutaway views of alternative exemplary urinary catheters for measuring radiation in accordance with aspects of this disclosure. FIG. 5A illustrates an exemplary urinary catheter 500 comprising an optical fiber lumen 503, an inflation lumen 505 and a urine drainage channel 507. The optical fiber lumen 503 may be used for sensor placement in the proximity of an inflated balloon. The inflation lumen 505 may be used to inflate the balloon. In an example implementation, the urinary catheter 500 may have a diameter of 4.7 mm, and the optical fiber lumen 503 may have a diameter of 1.3 mm. Variations of these diameters are also envisioned by this disclosure.

FIG. 5B illustrates another exemplary urinary catheter 510 comprising three optical fiber lumens 503, an inflation lumen 505 and a urine drainage channel 507.

FIG. 5C illustrates yet another exemplary urinary catheter 520 comprising three optical fiber lumens 503, an inflation lumen 505 and a urine drainage channel 507.

While the present system has been described with reference to certain implementations, it will be understood by those skilled in the art that various changes may be made and equivalents may be substituted without departing from the scope of the present system. In addition, many modifications may be made to adapt a particular situation or material to the teachings of the present disclosure without departing from its scope. Therefore, it is intended that the present method and/or system not be limited to the particular implementations disclosed, but that the present system will include all implementations falling within the scope of the appended claims.

As utilized herein the terms "circuits" and "circuitry" refer to physical electronic components (i.e. hardware) and any software and/or firmware ("code") which may configure the hardware, be executed by the hardware, and or otherwise be associated with the hardware. As used herein, for example, a particular processor and memory may comprise first "circuitry" when executing a first one or more lines of code and may comprise second "circuitry" when executing a second one or more lines of code. As utilized herein, "and/or" means any one or more of the items in the list joined by "and/or". As an example, "x and/or y" means any element of the three-element set {(x), (y), (x, y)}. In other words, "x and/or y" means "one or both of x and y". As another example, "x, y, and/or z" means any element of the seven-element set {(x), (y), (z), (x, y), (x, z), (y, z), (x, y, z)}. In other words, "x, y and/or z" means "one or more of x, y and z". As utilized herein, the term "exemplary" means serving as a non-limiting example, instance, or illustration. As utilized herein, the terms "e.g.," and "for example" set off lists of one or more non-limiting examples, instances, or illustrations. As utilized herein, circuitry is "operable" to perform a function whenever the circuitry comprises the necessary hardware and code (if any is necessary) to perform the function, regardless of whether performance of the function is disabled or not enabled (e.g., by a user-configurable setting, factory trim, etc.).

What is claimed is:

1. A urinary catheter, the urinary catheter comprising:
a plurality of scintillators; and
a plurality of optical fibers located in one or more optical fiber lumens that pass through the urinary catheter, wherein:
the urinary catheter comprises an inflation lumen, and
in a deflated state, a diameter of the inflation lumen is smaller than a diameter of each of the one or more optical fiber lumens.

2. The urinary catheter of claim 1, wherein a system comprises the urinary catheter, a plurality of light detection units, and a processor operable to determine the location of the radiation source.

3. The urinary catheter of claim 1, wherein a processor is configured to calculate a location of a radiation source by triangulation according to electrical signals from a plurality of light detection units.

4. The urinary catheter of claim 1, wherein the urinary catheter comprises a plurality of light detection units.

5. The urinary catheter of claim 1, wherein the urinary catheter comprises a plurality of fiducial markers embedded into walls of the urinary catheter in proximity to the plurality of scintillators.

6. The urinary catheter of claim 5, wherein the plurality of fiducial markers are located via an MRI machine after the urinary catheter is placed in a patient and prior to radiation therapy.

7. The urinary catheter of claim 1, wherein the plurality of scintillators is three scintillators and the plurality of optical fibers is three optical fibers.

8. The urinary catheter of claim 1, wherein the urinary catheter comprises a balloon for maintaining one end of the urinary catheter in a patient's bladder.

9. The urinary catheter of claim 1, wherein the urinary catheter comprises a balloon for expanding the urinary catheter near a tumor location.

10. The urinary catheter of claim 9, wherein the plurality of scintillators and the plurality of optical fibers are spread out when the balloon is expanded.

11. A urinary catheter, the urinary catheter comprising:
an afterloader catheter operable to carry a radiation source;
a plurality of scintillators; and
a plurality of optical fibers located in one or more optical fiber lumens that pass through the urinary catheter, wherein:
the urinary catheter comprises an inflation lumen, and
in a deflated state, a diameter of the inflation lumen is smaller than a diameter of each of the one or more optical fiber lumens.

12. The urinary catheter of claim 11, wherein a system comprises the urinary catheter, a plurality of light detection units, and a processor operable to determine a location of the radiation source, and wherein the location of the radiation source is input to an afterloader that is controlling the radiation source.

13. The urinary catheter of claim 11, wherein a processor is configured to calculate a location of the radiation source by triangulation according to electrical signals from a plurality of light detection units.

14. The urinary catheter of claim 11, wherein the urinary catheter comprises a plurality of light detection units.

15. The urinary catheter of claim 11, wherein the urinary catheter comprises a plurality of fiducial markers embedded into walls of the urinary catheter in proximity to the plurality of scintillators.

16. The urinary catheter of claim 15, wherein a position of each of the plurality of fiducial markers is determined via an MRI machine after the urinary catheter is placed in a patient and prior to radiation therapy.

17. The urinary catheter of claim 11, wherein the plurality of scintillators is three scintillators and the plurality of optical fibers is three optical fibers.

18. The urinary catheter of claim 11, wherein the urinary catheter comprises a balloon for maintaining one end of the urinary catheter in a patient's bladder.

19. The urinary catheter of claim 11, wherein the urinary catheter comprises a balloon for expanding the urinary catheter near a tumor location.

20. The urinary catheter of claim 19, wherein the plurality of scintillators and the plurality of optical fibers are spread out when the balloon is expanded.

* * * * *